(12) United States Patent
Lange et al.

(10) Patent No.: US 7,851,165 B2
(45) Date of Patent: Dec. 14, 2010

(54) SCREENING COMPOUNDS FOR ACTIVITY IN MODULATING CHLORIDE ION TRANSPORT

(75) Inventors: Philipp Lange, Bonn (DE); Jens C. Fuhrmann, Berlin (DE); Thomas Jentsch, Berlin (DE)

(73) Assignee: Pharmos Bioscience A/S, Herlev (DK)

( * ) Notice: Subject to any disclaimer, the term of this patent is extended or adjusted under 35 U.S.C. 154(b) by 0 days.

(21) Appl. No.: 12/086,726

(22) PCT Filed: Dec. 18, 2006

(86) PCT No.: PCT/EP2006/069829

§ 371 (c)(1),
(2), (4) Date: Jan. 14, 2009

(87) PCT Pub. No.: WO2007/071645

PCT Pub. Date: Jun. 28, 2007

(65) Prior Publication Data

US 2009/0170127 A1 Jul. 2, 2009

(30) Foreign Application Priority Data

Dec. 20, 2005 (GB) .................................. 0525898.3

(51) Int. Cl.
*G01N 33/566* (2006.01)
(52) U.S. Cl. .................. 435/7.1; 435/7.2; 435/7.21; 436/501
(58) Field of Classification Search ...................... None
See application file for complete search history.

(56) References Cited

U.S. PATENT DOCUMENTS

| 2003/0215787 A1 | 11/2003 | Yang et al. |
| 2004/0009915 A1 | 1/2004 | Chang et al. |
| 2004/0219511 A1 | 11/2004 | Liang |

FOREIGN PATENT DOCUMENTS

| WO | WO-02/059356 | 8/2002 |
| WO | WO-02/079414 | 10/2002 |

OTHER PUBLICATIONS

C. Blin-Wakkach et al., "Osteopetrosis, from mouse to man", *Medicine Sciences*, 20:1, pp. 61-67 (2004).
E. Cleiren et al., "Albers-Schonberg disease (autosomal dominant osteopetrosis, type II) results from mutations in the CICN7 chloride channel gene", *Human Molecular Genetics*, 10:25, pp. 2861-2867 (2001).
U. Kornak et al., "Loss of the ClC-7 Chloride Channel Leads to Osteopetrosis in Mice and Men", *Cell*, vol. 104, pp. 205-215 (Jan. 26, 2001).
P. Quarello et al., "Clinical Vignette: Severe Malignant Osteopetrosis Caused by a GL Gene Mutation", *Journal of Bone and Mineral Research*, 19:7, pp. 1194-1199 (2004).
A. Ramirez et al., "Identification of a Novel Mutation in the Coding Region of the Grey-Lethal Gene OSTM1 in Human Malignant Infantile Osteopetrosis", *Human Mutation*, vol. 23, pp. 471-476 (2004).
G.A. Rodan et al., "Therapeutic approaches to bone diseases", *Science*, vol. 289, pp. 1508-1514 (2000).
S.L. Teitelbaum et al., "Genetic regulation of osteoclast development and function", *Nature Review—Genetics*, vol. 4, pp. 638-649 (2003).
S.L. Teitelbaum et al., "Bone Resorption by Osteoclasts", *Science*, vol. 289, pp. 1504-1508 (2000).
H.C. Blair et al., "Passive chloride permeability charge coupled to $H^+$ATPase of avian osteoclast ruffled membrane", *American Physiological Society*, vol. 260, pp. C1315-C1324 (1991).
H.C. Blair et al., "Extracellular-matrix degradation at acid pH—Avian osteoclast acid collagenase isolation and characterization", *Biochem. J.*, 290(3), pp. 873-884 (1993).
H.C. Blair et al., "Osteoclastic Bone Resorption by a Polarized Vacuolar Proton Pump", *Science*, vol. 245, pp. 855-857 (1989).
H.C. Blair et al., "Recent Advances Toward Understanding Osteoclast Physiology", *Clinical Orthopaedics and Related Research*, No. 294, pp. 7-22 (1993).
Q. Al-Awqati et al., "Chloride Channels of Intracellular Organelles", *Current Opinion Cell Biology*, vol. 7, pp. 504-508 (1995).
T. Laitala et al., "Inhibition of Bone Resorption in Vitro by Antisense RNA and DNA Molecules Targeted against Carbonic Anhydrase II or Two Subunits of Vacuolar $H^{+-}$-ATPase", *J. Clin. Invest.*, vol. 93, pp. 2311-2318 (1994).
R. Kiviranta et al., "Impaired bone resorption in cathepsin K-deficient mice is partially compensated for by enhanced osteoclastogenesis and increased expression of other proteases via an increased RANKL/OPG ratio", *Bone*, vol. 36, pp. 159-172 (2005).
T.J. Jentsch et al., "Physiological Functions of CLC Cl- Channels Gleaned from Human Genetic Disease and Mouse Models", *Annu. Rev. Physiol.*, vol. 67, pp. 779-807 (2005).
T.J. Jentsch et al., "Molecular Structure and Physiological Function of Chloride Channels", *Physiol. Rev.*, vol. 82, pp. 503-568 (2002).
B. Nilius et al., "Volume-activated Cl- Channels", *Gen. Pharmac.*, 27(7), pp. 1131-1140 (1996).
M.E.M. Kelly et al., "Outwardly rectifying chloride current in rabbit osteoclasts is activated by hyposmotic stimulation", *Journal of Physiology*, 475(3), pp. 377-389 (1994).
H. Sakai et al., "Synergetic activation of outwardly rectifying Cl- currents by hypotonic stress and external Ca2+ in murine osteoclasts" *Journal of Physiology*, 515(1), pp. 157-168 (1999).
A.F. Weidema et al., "Electrophysiological characterization of ion channels in osteoclasts isolated from human deciduous teeth", *Bone*, 27(1), pp. 5-11 (2000).
A.B. Campos-Xavier et al., "Chloride channel 7 (CLCN7) gene mutations in intermediate autosomal recessive osteopetrosis", *Hum. Genet.*, vol. 112, pp. 186-189 (2003).

(Continued)

*Primary Examiner*—John D Ulm
(74) *Attorney, Agent, or Firm*—Edwards Angell Palmer & Dodge LLP; Peter C. Lauro, Esq.; Melissa Hunter-Ensor, Esq.

(57) ABSTRACT

A method for screening a test compound for activity in modulating the activity of the chloride channel ClC-7 either directly or by modulating the subcellular localization of Ostm1 comprises determining whether test compound inhibits the binding of Ostm1 to ClC-7. Compounds active in the screen are candidates for use in treating bone resorption conditions such as Osteoporosis by modulating the activity of osteoclasts.

14 Claims, 6 Drawing Sheets

OTHER PUBLICATIONS

R.J. Daniels et al., "Sequence, structure and pathology of the fully annotated terminal 2 Mb of the short arm of human chromosome 16", *Human Molecular Genetics*, 10(4), pp. 339-352 (2001).

O. Scheel et al., "Voltage-dependent electrogenic chloride/proton exchange by endosomal CLC proteins", *Nature*, vol. 436, pp. 424-427 (2005).

T.J. Jentsch et al., "Physiological functions of CLC Cl- channels gleaned from human genetic disease and mouse models", *Annu. Rev. Physiol.*, vol. 67, pp. 779-807 (2005).

T.J. Jentsch et al., "CLC chloride channels and transporters", *Current Opinion in Neurobiology*, vol. 15, pp. 319-325 (2005).

A. Picollo et al., "Chloride/Proton Antiporter Activity of Mammalian CLC Proteins CIC-4 and CIC-5", *Nature*, vol. 436, pp. 420-423 (2005).

A. Accardi et al., "Secondary active transport mediated by a prokaryotic homologue of CIC Cl- channels", *Nature*, vol. 427, pp. 803-807 (2004).

N. Chalhoub et al., "Grey-lethal mutation induces severe malignant autosomal recessive osteopetrosis in mouse and human", *Nature Medicine.*, 9(4), pp. 399-406 (2003).

D. Kasper et al., "Loss of the chloride channel CIC-7 leads to lysosomal storage disease and neurodegeneration", *The EMBO Journal.*, vol. 24, pp. 1079-1091 (2005).

R.M. Van Der Hee et al., "Comparison of 3 AT1 receptor binding assays: filtration assay, ScreenReady Target, and WGA Flashplate", *Journal of Biomolecular Screening,*, 10(2), pp. 118-126 (2005).

K. Crane et al., "Development of a homogeneous binding assay for histamine receptors", *Analytical Biochemstry*, vol. 335, pp. 42-49 (2004).

P. Sorensen et al., "Identification of protein-protein interfaces implicated in CD80-CD28 costimulatory signaling", *The Journal of Immunology*, vol. 172, pp. 6803-6809 (2004).

M.A. Cooper et al., "Label-free screening of bio-molecular interactions", *Anal Bioanal. Chem.*, vol. 377, pp. 834-842 (2003).

G.J. Parker et al., "Development of High Throughput Screening Assays Using Fluorescence Polarization: Nuclear Receptor-Ligand-Binding and Kinase/Phosphatase Assays", *J. Biomol. Screen*, vol. 5, pp. 77-88 (2000).

R. Seethala et al., "Fluorescence Polarization Competition Immunoassay for Tyrosine Kinases", *Methods*, vol. 22, pp. 61-70 (2000).

R. Rigler et al., "Specific binding of proinsulin C-peptide to human cell membranes", *PNAS*, 96(23), pp. 13318-13323 (1999).

Y. Liu et al., "Screening of drugs by FRET analysis identifies inhibitors of SARS-CoV 3CL protease", *Biochemical and Biophysical Research Communications*, vol. 333, pp. 194-199 (2005).

D. Klostermeier et al., "A three-fluorophore FRET assay for high-throughput screening of small-molecule inhibitors of ribosome assembly", *Nucleic Acids Research*, 32(9), pp. 2707-2715 (2004).

B. Sharma et al., "Competitive Binding Assay Using Fluorescence Resonance Energy Transfer for the Identification of Calmodulin Antagonists", *Bioconjugate Chemistry*, vol. 16, pp. 1257-1263 (2005).

B. Zhang et al., "Design of FRET-based GFP probes for detection of protease inhibitors", *Biochemical and Biophysical Research Communications*, vol. 323, pp. 674-678 (2004).

C. Tahtaoui et al., "On the Use of Nonfluorescent Dye Labeled Ligands in FRET-Based Receptor Binding Studies", *Journal of Medicinal Chemistry*, vol. 48, pp. 7847-7859 (2005).

A. Pramanik et al., "Ligand-Receptor Interactions in the Membrane of Cultured Cells Monitored by Fluorescence Correlation Spectroscopy", *Biol. Chem.*, vol. 382, pp. 371-378 (2001).

T. Fischer et al., "Promotion of $G\alpha i3$ subunit down-regulation by GIPN, a putative E3 ubiquitin ligase that interacts with RGS-GAIP", *PNAS*, 100(14), pp. 8270-8275 (2003).

V. Rajapurohitam et al., "The Mouse Osteopetrotic Grey-Lethal Mutation Induces a Defect in Osteoclast Maturation/Function", *Bone*, 28(5), pp. 513-523 (2001).

C.M. Pickart et al., "Mechanisms Underlying Ubiquitination", *Annu. Rev. Biochem.*, vol. 70, pp. 503*533 (2001).

S.M. Stobrawa et al., "Disruption of CIC-3, 1 Chloride Channel Expressed on Synaptic Vesicles, Leads to a Loss of the Hippocampus", *Neuron.*, vol. 29, pp. 185-196 (2001).

Brandt et al., "CIC-6 and CIC-7 are two novel broadly expressed members of the CLC chloride channel family", *FEBS Letters*, vol. 377, pp. 15-20 (1995).

T. Nishi et al., "Molecular Cloning and Expression of Three Isoforms of the 100-kDa a Subunit of the Mouse Vacuolar Proton-translocating ATPase", *The Journal of Biological Chemistry*, 275(10), pp. 6824-6830 (2000).

J.C. Scimeca et al., "The Gene Encoding the MJouse Homologue of the Human Osteoclast-Specific 116-kDa V-ATPase Subunit Bears a Deletion in Osteosclerotic (oc/oc) Mutants", *Bone*, 26(3), pp. 207-213 (2000).

Y.P. Li et al., "Atp6i-deficient mice exhibit severe osteopetrosis due to loss of osteoclast-mediated extracellular acidification", *Nature Genetics*, vol. 23, pp. 447-451 (1999).

A. Frattini et al., "Chloride Channel *ClCN7* Mutations Are Responsible for Severe Recessive, Dominant, and Intermediate Osteopetrosis", *Journal of Bone and Mineral Research*, vol. 18, pp. 1740-1747 (2003).

A. Frattini et al., "Defects in TCIRG1 subunit of the vacuolar proton pump are responsible for a subset of human autosomal recessive osteopetrosis", *Nature Genetics*, vol. 25, pp. 343-346 (2000).

U. Kornak et al., "Mutations in the a3 subunit of the vacuolar $H^+$-ATPase cause infantile malignant osteopetrosis", *Human Molecular Genetics*, 9(13), pp. 2059-2063 (2000).

B.F. Boyce et al., "Bad bones, grey hair, one mutation", *Nature Medicine*, 9(4), pp. 395-396 (2003).

M. Fukuda et al., "Lysosomal Membrane Glycoproteins. Structure, Biosynthesis, and Intracellular Trafficking", *The Journal of Biological Chemistry*, 266(32), pp. 21327-21330 (1991).

E.L. Eskelinen et al., "At the acidic edge: emerging functions for lysosomal membrane proteins", *Trends in Cell Biology*, 13(3), pp. 137-145 (2003).

S. Schaller et al., "Interactions between the full complement of human RNA polymerase II subunits", *FEBS Letters*, vol. 461, pp. 253-257 (1999).

R. Estevez et al., "Barttin is a Cl- channel $\beta$-subunit crucial for renal Cl- reabsorption and inner ear $K^+$—secretion", *Nature*, vol. 414, pp. 558-561 (2001).

Q. Zhao et al., "A novel assay to identify entry inhibitors that block binding of HIV-1 gp120 to CCR5", *Virology*, vol. 326, pp. 299-309 (2004).

G. Stenbeck et al., "Formation and function of the ruffled border in osteoclasts", *Cell & Developmental Biology*, vol. 13, pp. 285-292 (2002).

O. Benichou et al., "Mapping of Autosomal Dominant Osteopetrosis Type II (Albers-Schonberg Disease) to Chromosome 16p13.3", *Am. J. Hum. Genet.*, vol. 69, pp. 647-654 (2001).

Schaller et al., "The Chloride Channel Inhibitor N53736 Prevents Bone Resorption in Ovariectomized Rats Without Changing Bone Formation", *Journal of Bone and Mineral Research*, 19(7), pp. 1144-1153 (2004).

SCREENING COMPOUNDS FOR ACTIVITY IN MODULATING CHLORIDE ION TRANSPORT

CROSS-REFERENCE TO RELATED APPLICATIONS

This application is the U.S. national phase, pursuant to 35 U.S.C. §371, of PCT international application Ser. No. PCT/EP2006/069829, filed Dec. 18, 2006, designating the United States and published in English on Jun. 28, 2007, as publication no. WO 2007/071645, which claims priority to G.B. application Ser. No. 0525898.3, filed Dec. 20, 2005. The entire contents of the aforementioned patent applications are incorporated herein by this reference.

The present invention relates to methods for screening compounds for activity in modulating chloride ion transport via ClC-7 or modulating subcellular localisation of Ostm1. Compounds that successfully modulate such chloride ion transport will be candidates for use in the study or treatment of osteoclast related diseases such as osteoporosis and other osteoclastic metabolic diseases such as Paget's disease, steroid induced osteoporosis and cancer subtypes such a bone metastasis. Osteoporosis is defined as skeletal fragility characterized by reduced bone mass and micro-architectural deterioration, which leads to increased fractures. The majority of osteoporotic fractures occur in older women after menopause (1).

Two cell types are responsible for the bone remodelling processes: the bone forming osteoblast and the bone degrading osteoclast (2, 3). The osteoclasts attach to the bone matrix and form the bone-resorbing compartment and the ruffled border by exocytosis of lysosomes (4). Dissolution of bone by acidification of the resorption compartment is mediated by an active transport of protons through the osteoclastic V-type $H^+$ ATPase (5-8). At the same time, a passive transport of chloride through chloride conductances (channels and/or electrogenic coupled transporters) preserves the electroneutrality (9). Prevention of chloride transport will lead to a rapid hyperpolarization of the membrane, preventing further secretion of protons, thus resulting in an inhibition of further bone resorption (10, 11). Drugs inhibiting the acidification employ a different mode of action than existing treatments for bone metabolic diseases.

Chloride channels and transporters comprise a large group of transmembrane proteins positioned in the plasma membrane and in intracellular vesicles. Their roles vary from the control of secretion and absorption of salt, regulation of membrane potentials, organellar acidification and cell volume homeostasis (12, 13). Three different structural families of chloride channels have been characterized: the CLC voltage-gated chloride channels and chloride proton exchangers, the ligand-gated chloride channels containing the glycine receptor and the γ-aminobutyric acid receptor, and the CFTR (cystic fibrosis transmembrane conductance regulator). Moreover, two additional families of putative chloride channels have been identified: the CLIC (chloride intracellular channels) and the CLCA calcium activated chloride channels. Another chloride channel, called volume regulated anion channel (VRAC) and the molecular identity of which has not been established yet, has been identified by electrophysiology in most mammalian cells (14) including the osteoclasts (15-17).

The CLIC, CLCA and VRAC functions are not very well understood yet, whereas the CLC channels and transporters have been characterized through analysis of mutations leading to genetic disorders and generation of knock-out mice (13). Mutations in the CLCN7 gene are responsible for various forms of osteopetrosis: the Autosomal Dominant Osteopetrosis II (ADOII), cases of Autosomal Recessive Osteopetrosis (ARO) and of an intermediate form of ARO (IARO) (18-22). Furthermore the disruption of Clcn7 leads to severe osteopetrosis in mice, with approximately 700% more bone (22). Among the ClCs, ClC-0, ClC-1, ClC-2 and ClC-Ks have been shown to be proper chloride channels (23-25), whereas ClC-4 and ClC-5 have been shown to be chloride proton exchangers (23, 26) where it is proposed that in the case of the exchanger, the ClCs transport one proton for two chloride (27). This was shown by electrophysiology and acidification measurements.

ClC-7 (the expression product of the CLCN7 gene) as well as ClC-6 have not been characterized by electrophysiology, thus it has not been clarified whether they are chloride channels or chloride proton exchangers. In both cases, the role of ClC-7 remains the same (acidification of the resorption lacunae) and its inhibition leads to increased bone density.

Methods for screening compounds for the ability to modulate the transport of chloride ions by ClC-7 have been proposed in WO02/059612 and in WO02/059356. These methods were based on the measurement of acidification as a proxy for chloride ion transport in a cell or an organelle. However, many inhibitors of transport via ClC-7 are likely also to inhibit other chloride channels or transporters. Hence it is necessary to counter screen against other chloride channels to try to find a selective inhibitor. Selectivity for action directly on ClC-7 may be difficult to achieve due to the sequence homology and structural conservation of CLC proteins.

The present invention relates to a new approach in which a newly discovered dependency of ClC-7 on another protein, (Ostm1—Osteopetrosis-associated transmembrane protein 1, the product of the OSTM1 gene), for functional transport of chloride is exploited. This dependency is mediated by an interaction (direct or indirect) between ClC-7 and Ostm1. Thus, it has now been discovered that additional molecules modulate ClC-7 function, among others the protein Ostm1, which is therefore also required for normal osteoclast function.

Accordingly Ostm1 inhibitors (e.g. compounds that inhibit Ostm1 expression), or compounds disrupting the interaction between Ostm1 and ClC-7 may be relevant pharmaceutical compounds for the treatment or prevention of osteoclast related diseases.

Ostm1 is a transmembrane protein of previously unknown function. Mutations in the OSTM1 gene cause a severe osteopetrosis syndrome, as was shown for the spontaneous mouse mutant called 'grey lethal' (28) and human patients (28, 29).

Similarly, mutations in ClC-7, a late endosomal/lysosomal member of the ClC family of chloride channels and transporters (12, 25), cause osteopetrosis (22) and lysosomal storage disease (30) in man and mice.

We have now found that both proteins co-localise in late endosomes and lysosomes of various tissues, as well as in the ruffled border of bone-resorbing osteoclasts. Co-immunoprecipitations reveal that ClC-7 and Ostm1 form a molecular complex and suggest Ostm1 as a novel 5-subunit of ClC-7. Ostm1 needs ClC-7 to reach lysosomes, where its highly glycosylated luminal domain is cleaved. The protein, but not RNA, levels of ClC-7 are greatly reduced in grey-lethal mice lacking Ostm1 and vice versa, suggesting that their interaction is important for protein stability. As the level of ClC-7 protein is decreased below 10% in Ostm1-deficient tissues and cells including osteoclasts, Ostm1 mutations can now be seen to cause osteopetrosis by impairing the acidification of the osteoclast resorption lacuna that depends on ClC-7 (22). The finding that grey-lethal mice, just like ClC-7 knock-out mice (30), display lysosomal storage and neurodegeneration in addition to osteopetrosis implies a more general importance of ClC-7/Ostm1 complexes.

The present invention now provides a method for screening a test compound for activity in modulating chloride transport via ClC-7, which comprises determining whether or the extent to which the test compound prevents or inhibits the binding of Ostm1 to ClC-7.

In an alternative realization, the present invention provides a method for screening a test compound for activity in modulating the subcellular localization of Ostm1 which comprises determining whether or the extent to which the test compound prevents the binding of Ostm1 to ClC-7. As the subcellular localisation of Ostm1 is influenced by its interaction with ClC-7 and modulates ClC-7 stability, interference in the mutual binding of ClC-7 and Ostm1 is likely to result in a localization behaviour that is changed by the test compound.

In a further aspect, the invention provides a method for screening a test compound for activity in modulating interaction between ClC-7 and Ostm1, which method comprises determining whether or the extent to which the test compound prevents binding of Ostm1 to ClC-7.

In either aspect, the invention may be practised to screen numerous compounds for the desired property.

Because other chloride channels are not known to interact with Ostm1 (and we have demonstrated a lack of interaction between Ostm1 and ClC-3 and ClC-6, respectively), a blocker of the interaction between Ostm1 and ClC-7 is more likely to provide selectivity in decreasing ClC-7 functional activity with respect to other chloride channels and transporters than a compound selected simply for its direct effect on ClC-7 alone. It is thought that the interaction between ClC-7 and Ostm1 is direct rather than through some intermediate protein or other molecule, and evidence for that is presented below. However, cell based methods are described herein that should be effective even if the interaction is indirect.

Such a method may be practised by exposing ClC-7, or a fragment thereof capable of binding Ostm1, to Ostm1 or to a fragment thereof capable of binding ClC-7, said exposure being in the presence of said test compound, and determining whether or the extent to which binding between the ClC-7 or fragment thereof and the Ostm1 or fragment thereof is prevented or disrupted.

Both Ostm1 and ClC-7 are expressed and functional in very many organisms. In practising the invention, one may use Ostm1 and ClC-7 selected from those of any organism in which both are expressed, particularly any mammal, e.g. rodent (especially mouse) or human. Preferably, the Ostm1 used and the ClC-7 used should come from the same organism, but ones of different origin that bind one another are satisfactory. The use of Ostm1 and ClC-7 which are human is preferred. Amongst non-human Ostm1 and ClC-7, those that are more closely homologous to the human proteins are preferred.

In what follows, we refer to fragments of ClC-7 which are capable of binding Ostm1 and to fragments of Ostm1 which are capable of binding ClC-7 as 'binding fragments'.

In said exposure step one of said ClC-7 or binding fragment thereof and Ostm1 or binding fragment thereof may be immobilised to a solid support and the other thereof and said test compound may be in solution. Such solid supports may be multi-well plates, test strips, beads, or other supports known or conventional in the art or equivalent thereto.

The ClC-7 or binding fragment thereof or the Ostm1 or binding fragment thereof which is in solution may bear a detectable label such as a radio-label, an enzyme label, a label which is able to be stimulated to emit light, e.g. as fluorescence.

The screening method may also be performed such that all of the ClC-7 or binding fragment thereof, the Ostm1 or binding fragment thereof, and the test compound are in solution in said exposure step.

Optionally, in homogeneous or non-homogeneous systems, said ClC-7 or binding fragment thereof and said Ostm1 or binding fragment thereof each bear a label, and the proximity of the said labels may be detectable.

Alternatively, ClC-7 and Ostm1 are present in situ in a cell or intracellular organelles which can be lysosomes, endosomes, the endoplasmic reticulum, the Golgi apparatus, the osteoclastic plasma membrane facing the resorption lacuna or the plasma membrane in other cell types. Again, each of the ClC-7 and the Ostm1 bear a label, and the proximity of the said labels may be detectable.

In such screening methods, the concentration of the test compound may suitably be from 10 pM to 10 µM, e.g. from 100 pM to 10 nM, e.g. about 1 nM.

According the invention it has now been discovered that Ostm1 is important for ClC-7 function. Therefore pharmaceutical modalities which disrupt this interaction and thereby inhibit ClC-7 are of interest as potential treatment or prevention agents in connection with diseases including osteoclast related bone diseases, such as osteoporosis and other osteoclastic related diseases. The described screening methods may be used in drug development or in confirming the mode of action of a known therapeutic agent.

In a further aspect, the invention relates to the use of a compound identified as a blocker of the interaction between ClC-7 and Ostm1 by a said screening method in the treatment, prevention or alleviation of an osteoclast related bone disease in a subject.

Other objects and uses of the invention will be apparent to the person skilled in the art from the following detailed description and examples.

Optionally, one may further screen to select compounds that do not block interaction between Ostm1 and some other chosen molecule or do not block interaction between ClC-7 and some other chosen molecule.

Optionally, one may further screen to select compounds that do not block interaction between proteins in general, for instance by screening for lack of blocking effect on a protein pair such as CLC-K and barttin (a chloride channel β-subunit not related to Ostm1) (61).

Numerous screening methods may be used in order to identify compounds that inhibit ClC-7/Ostm-1 interaction, thus inhibiting bone resorption by down-regulation of ClC-7 levels or activity. The assay can consist of a binding test between ClC-7 and Ostm1 in the presence of a test compound that potentially can inhibit this interaction.

Alternatively, it can comprise a preliminary screening assay that identifies compounds that bind to one of the proteins (ClC-7 or Ostm1) present either in full length form or as only a part of such a protein involved in the interaction (a binding fragment), followed by further testing for the disruption of the interaction with the second partner.

Alternatively, it can comprise an in vivo screening assay that identifies compounds that inhibit targeting of Ostm1 to late endosomes/lysosomes and co-localization with ClC-7 and lamp-1 (lysosomal-associated membrane protein), based on the finding that Ostm1 requires Clc-7 for lysosomal localisation as demonstrated in FIG. 2 below. This may be practised on wild type cells (looking at endogenous Ostm1 or in ClC-7$^{-/-}$ deficient fibroblasts (for over-expression of epitope tagged ClC-7 and Ostm1).

Suitable methods can be applied using full-length proteins or using fragments of the proteins that are involved in the interaction or using one protein in full length form and the other as a binding fragment.

As exemplified below (see Examples 1-3), immuno-precipitation and His-tag purification can be used in order to test the interaction of the proteins or suitable fragments in the presence of suitable test compounds. Thus, in an immunoprecipitation screening assay, ClC-7 and Ostm1 (independently as whole protein or as a binding fragment) may be incubated with a test compound and may then be immuno-precipitated using an antibody specific for either ClC-7 or Ostm1. Co-immunoprecipitation may be detected in various ways. The precipitate may be loaded on a gel and run and detected by Western blotting with a labelled antibody to the other of said proteins. The precipitate may be washed and then stained with a labelled antibody to the other of the proteins. Alternatively, the interaction partner can be radioactively labelled and detected by SDS-page or radioactive counting.

His-tag precipitation may be carried out as follows. ClC-7, Ostm1 or a binding fragment of one of them is recombinantly expressed in a modified form in which it is extended by a sequence of His amino acids, e.g. His$_6$ (SEQ ID NO: 1), suitably at the C-terminal or the N-terminal. This enables the His-tagged protein to be captured to beads such as Ni-NTA beads. Then, exposure of the loaded beads to the other protein or binding fragment and the test compound will result (if the test compound is ineffective) in binding of both proteins to the beads. The presence of both proteins on the beads after a suitable washing step can be determined by staining the beads directly with a labelled antibody or by removing the bound proteins from the beads and then conducting a Western blot to detect the presence of the said other protein or fragment (or radioactive detection, as above).

A high throughput screening (HTS) compatible format for a screen can be provided as an ELISA system as described in ref. 62 (Zhao et al). One of the proteins (or binding fragments thereof) is fixed to a plate or equivalent solid support either directly, as by using a purified protein and a Maxiprop™ plate, or indirectly, as by using an antibody against Ostm1 or ClC-7 (that can be bound to a streptavidin plate if biotinylated). An extract with the interaction partner ClC-7 or Ostm1 respectively and selected test compound is incubated on each well of the plate. After washing, a secondary antibody is used to detect the interaction partner using an enzyme labelled (e.g. peroxidase (POD) labelled) specific antibody or a specific antibody recognized by an anti-species, e.g. anti rabbit or anti mouse POD antibody. The presence of the labelled antibody is detected, e.g. a POD antibody is detected with a 3,3',5,5'-tetramethylbenzidine (TMB) substrate. The coloration indicates the presence of the interaction partner. If the compound is able to disrupt this interaction, the coloration is lost. The optical density can be detected in an ELISA reader in 96 well plates and thus this assay can be optimised for HTS.

A similar assay can be developed using Flashplates and radioactive labels (31). The Flashplates™ (Perkin Elmer) are 96 well microplates permanently coated with a thin layer of scintillant. The principle is similar to the ELISA assay described above. One of the proteins (or a binding fragment thereof) is fixed to the wells. A specific WGA Flashplate that binds to glycosylated proteins can be used to fix Ostm-1. The second protein needs to be radioactively labelled. This can be achieved by cultivating cells that over express the protein in a medium containing S$^{35}$ Methionine and S$^{35}$ Cysteine. Alternatively, it may be bound with a radio-labelled antibody. After incubation with the compounds and washing, the radioactivity is measured using a system such as a Wallac counter. If the compound disrupts the interaction, the radioactive protein is too far from the scintillant to activate it.

Another suitable methodology using radioactivity and proximity is the SPA system (32, 33): scintillation proximity assay. Beads with anti mouse or anti rabbit antibodies are available as well as Nickel chelate beads that can fix His tag proteins. These beads are used to fix one protein or a binding fragment thereof. For instance, one may bind the protein to an antibody for that protein generated in a mouse and bind the complex to the beads by the anti mouse antibody. The second protein or a binding fragment thereof is radiolabelled as described above and is incubated with the beads and the compounds to test. As in the Flashplates assay the scintillant contained in the beads is only activated upon binding of the radiolabelled protein.

Other methods of detection of protein/protein interactions are available and can be used to detect if compounds are able to disrupt the interaction. They include a range of label-free interaction screening methodologies (34). These use optical biosensor (Affinity Sensors, Biacore, HTS biosystems, IBIS, SRU Biosystems), acoustic biosensor (Akubio) or microcalorimetry (MicoCal, Thermometric, Calorimetry sciences Corp., 3D Pharmaceuticals, Vivactiss) based methods.

Only the Biacore (surface plasmon resonance) system will be described here in detail, but the other methodologies can be applied as well. One of the proteins or a binding fragment thereof is fixed to a metal surface, preferably gold on a prism. The bound protein is exposed to the test compound and the other protein or a binding fragment thereof. By directing polarised light onto the prism, the critical angle of reflection from behind the surface is recorded. The angle of this reflected light is dependent on the mass of the molecules at the surface layer, so that the method can detect the binding of a second protein and the displacement or prevention of this binding by compounds.

The parts of the respective proteins involved in the interaction between the full length proteins have yet to be determined. However, this information can be gained by performing any of the above described techniques to detect the interaction between fragments of ClC-7 and Ostm1 or between ClC-7 and fragments of Ostm1. One may recombinantly express only parts of the coding sequence of one or both proteins (for example only the intracellular domain or the extracellular domain or the various transmembrane domains alone or in association). The interaction tests described above may be performed on these fragments in order to identify which fragments are necessary to maintain the interaction. One may also detect interacting domains by testing fragments of ClC-7 and Ostm1 in the yeast-two-hybrid technique.

A fluorescence polarisation assay (35, 36) may be performed between a full-length protein (Ostm1 or ClC-7) and a suitably small fragment of the interaction partner (ClC-7 or Ostm1 respectively) that is fused to a fluorophore (for example fluorescein). When the small fragment is not bound and is excited with a polarized light, it will depolarise the light due to the rotation of the fluorophore. When the small fragment binds to the full length interaction partner, the light will remain polarized. Thus compounds that disrupt the interaction can be screened in this assay. The light emitted needs to be detected through a polarisation filter. HTS compatible readers are available at Tecan, BMG LabTechnologies, LJL Biosystems and Jolley Consulting and Research Inc.

A filtration assay may be used as generally described in Ref. (31).

A filtration assay may consist also of an interaction assay between full-length protein (Ostm1 or ClC-7) and a binding fragment of the interaction partner (ClC-7 or Ostm1 respectively) that is fused to a fluorophore (for example fluorescein) or is radiolabelled. After incubation of the interaction partners in a buffer with the compound to test, the preparation is centrifuged on a membrane that allows the small fragment to go through but not the full length protein. If the fragment interacts with the full-length protein, it will not go through the membrane either and the supernatant will remain fluorescent or radioactive.

Fluorescence (or Forster) Resonance Energy Transfer (FRET) is based on non-radiative energy transfer between a donor and an acceptor (37, 38, 39, 40, 41). The donor is fixed to one of the proteins (or a binding fragment) close to its site of interaction. It can be a recombinantly expressed ClC-7 or a fragment retaining the site of interaction with Ostm1 fused to a first fluorophore (e.g. cyan fluorescent protein—CFP). The second protein is fused to an acceptor close to its site of interaction or only a fragment that interacts with the protein is used. It can be the domain of Ostm1 that interacts with ClC-7. The Ostm1 or binding fragment thereof may be fused to an acceptor such as yellow fluorescent protein—YFP. A lot of different acceptor and donor pairs are widely used and all can be used in this assay. The acceptor can be fluorescent or not and the FRET is detected by the appearance of sensitized fluorescence of the acceptor, by the intensity ratio change of donor/acceptor, by the fluorescence decrease of the donor, or by changes in the fluorescence lifetime of the donor. Both fusion-proteins are recombinantly expressed, extracts are prepared and they are incubated together with or without (control) the compounds to test. Alternatively, the assay may be performed in live or fixed cells. Less preferably, non-protein chromophores may be chemically linked to the proteins for practising in vitro methods.

When CFP is excited at 452 nm, it emits a fluorescence wavelength at 505 nm that is an excitation wavelength for YFP. YFP will in turn emit at 527 nm if it is in close proximity to CFP, thus only when ClC-7 and Ostm1 fragments interact. If a compound disrupts the interaction, it will also disrupt the YPF excitation and emission at 527 nm (35).

Non fluorescent acceptors can found in other pairs of donor-acceptors such as EDANS/Dabcyl or pinacyanol/EGFP (42). In this case, upon interaction leading to a close proximity of pinacyanol to EGFP (both fused to one interaction partner), the EGFP fluorescence at 510 nm will decrease accordingly.

Changes in the fluorescence of the donor or the acceptor may be measured as an intensity measurement or in a time resolved manner. The recordings can be done in a spectrofluorometer (Molecular Devices) and can be set-up as an HTS format.

The above technique can be applied on living cells using Fluorescence Correlation Spectroscopy (Evotec)(43). This method uses confocal microscopy and can detect if a labelled ligand can bind to its receptor in cells. This can be adapted also for in situ detection of protein-protein interaction using the FRET method described above. To identify compounds that inhibit targeting of Ostm1 to late endosomes/lysosomes and co-localization with ClC-7 and lamp1 therein the following as well as other methods can be applied. Endogenous or over expressed ClC-7 and Ostm1 protein can be monitored indirectly by incubation of live or fixed cells with anti-ClC-7 and anti-Ostm1 antibodies followed by incubation with matching secondary antibodies coupled to a fluorochrome or enzyme. Alternatively fluorescent proteins fused to ClC-7 or Ostm1 can be monitored directly after over expression in cells. The potential of a given compound to inhibit proper targeting of Ostm1 to late endosomes/lysosomes, which is shown herein to depend on binding to ClC-7, can be measured as the amount of co-localization of Ostm1 with lysosomal proteins such as lamp1. The data acquisition can be performed using microscopy or confocal microscopy of live or fixed cells in microtiter plates.

BRIEF DESCRIPTION OF THE DRAWINGS

The invention will be further described and illustrated with reference to the accompanying drawings, in which:

FIG. 1 part (a) shows an annotated schematic of the mouse Ostm1 protein in which the symbols represent the following: Black box, hydrophobic stretch; Y, consensus site for N-linked glycosylation; *, cysteine; Arrow, predicted signal peptide cleavage site; Dashed, proposed RING-finger domain (44); AB, antibody binding site; Lines, truncated proteins predicted from human OSTM1 mutations (28, 29);

FIG. 1 part (b) shows a topology model of the Ostm1 protein in which the arrow points to an approximate cleavage site in lysosomal Ostm1;

FIG. 1 parts (c)-(f) show Western blots obtained as described below.

Row (a): Fibroblast stained for endogenous Ostm1 and lamp-1. The third panel shows the overlay, with higher magnification in the fourth panel.

P Row (b) Ostm1-transfected fibroblasts showed a reticular and perinuclear Ostm1 staining that co-localised poorly with lamp-1.

Rows (c) and (d): In fibroblasts co-transfected with Ostm1 and ClC-7, Ostm1 co-localised with lamp-1 (c) and ClC-7 (d).

Row (e): Co-transfecting Ostm1 with ClC-6 did not lead to a lysosomal localisation of Ostm1, nor to a significant co-localisation. In (b-e), $Clcn7^{-/-}$ fibroblasts were used to avoid effects of endogenous ClC-7, but similar results were seen in HeLa cells. Scale bar indicates 8.5 µm for (a), 10 µm for (b-e), and 1.7 µm for enlargements (right).

part (a) Western blot for Ostm1 in WT, $Clcn7^{-/-}$ and grey-lethal (gl) brain.

part (b) Subcellular distribution of Ostm1 in WT and Clcn7 mice, part (c) Deglycosylation of WT lysosomal and Clcn7 ER/endosomal fractions, part (d) Co-immunoprecipitation of a ClC-7/Ostm1 complex.

FIG. 4 shows immunofluorescence images of cerebellar Purkinje cells in panels (a) and (b) and of osteoclasts in situ in panels (c)-(e). In (a-e), overlays (right) are shown with TOTO staining (blue) for nucleic acids. Scale bar in (a), 10 µm for (a-e). Panel (f) shows Western blots which are quantified in panel (g)—Age, P11-P33. Error bars, SEM. n=3-9, except for ClC-3 in bone (n=2). 'h' and 'i' are methylene blue-stained histological sections showing retinal degeneration in gl (h) but not in WT (i) mice at age P31. A section of hippocampus showing neurodegeneration in the CA3 region (arrows) of a P47 gl mouse revealed by anti-NeuN staining (Scale bar, 100 µm) is seen in panel (j).

Figure 1:
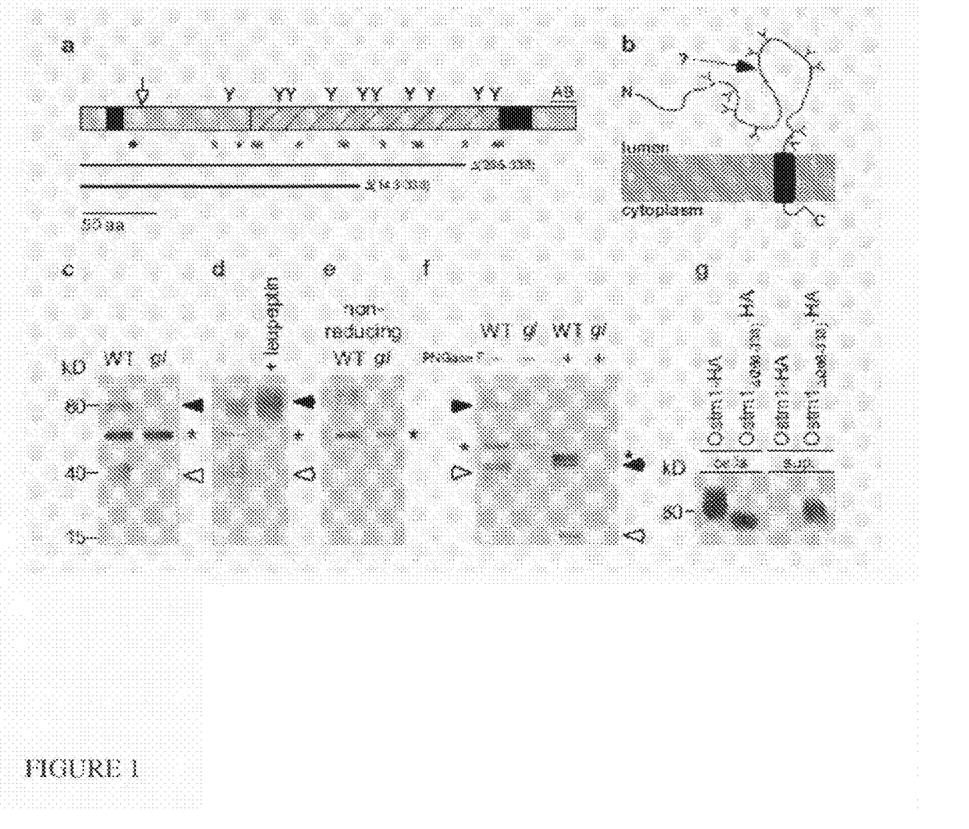

FIG. 1 part (c) shows a Western blot of brain membrane proteins revealing an Ostm1 band at ~80 kD (filled arrowhead) and a doublet at ~35-45 kD (open arrowhead) that were absent in grey-lethal (gl) mice, an osteopetrotic mouse mutant (45) carrying a deletion of the Ostm1 promoter and exon 1 (28).

Antibodies against Ostm1 (peptide C-LKSSTSFA-NIQENAT (SEQ ID NO: 2)) have been raised in guinea pigs and rabbits and tested for specificity on KO tissues.

In FIG. 1 part (d), incubation of fibroblasts with leupeptin increased the proportion of the large Ostm1 species. Similar results were obtained with E64, an inhibitor of cathepsin B, L and S (data not shown). Thus, incubating cells with protease inhibitors increased the proportion of the large band at the expense of the smaller ones (FIG. 1 part (d)), indicating that the small form was produced by proteolytic cleavage of the ~80 kD protein. The apparent sizes of Ostm1 species suggest a cleavage roughly in the middle of the protein (FIG. 1 part (b)).

In FIG. 1 part (e), Western blots of brain proteins separated by non-reducing SDS-PAGE showed a single large Ostm1-specific band, in contrast to the large and small forms observed under reducing conditions. Thus, the cleaved fragments might be linked by disulfide bonds between some of the cysteines that abound in the luminal domain of Ostm1 (FIG. 1 part (a)).

Recent work proposed an E3 ubiquitin ligase function for Ostm1 (cloned independently as GIPN) (44). The stretch between the amino- and carboxy-terminal hydrophobic regions of Ostm1 (FIG. 1 part (a)) displayed weak homology to RING-finger proteins and was suggested to be cytosolic (44). However, this stretch (and no other part of the protein) contains several consensus sites for N-linked glycosylation. In the Western blot of FIG. 1 part (f), deglycosylation with PNGaseF reduced the sizes of all Ostm1-species detected under reducing conditions, demonstrating that several or all of these sites are used. The observed glycosylation placed the hypothetical RING-finger domain (44) into the lumen of endoplasmic reticulum (ER), a localisation difficult to reconcile with the cytosolic/nucleoplasmic activity of ubiquitin ligases (46). The disappearance in transfected cells of an HA-epitope added to the amino-terminus indicated the presence of a cleavable signal peptide (data not shown). FIG. 1 part (f) also revealed that the apparent molecular weight of the largest deglycosylated band roughly agreed with the prediction from the Ostm1 reading frame (~37 kDa). As deglycosylation of the small species yielded a single band, the doublet is due to non-uniform glycosylation.

We also investigated an Ostm1 mutant truncated before the second hydrophobic stretch, predicted to serve as a transmembrane domain. In FIG. 1 part (g) there is shown a Western blot of cells (lanes 1+2) and supernatants (lanes 3+4) of HEK293 cells expressing Ostm1 (lanes 1+3) or a truncated form (lanes 2+4) mimicking a human mutation (44). Both proteins carried a C-terminal HA-epitope for detection. This mutant, but not WT Ostm1, was secreted into the supernatant of transfected cells (FIG. 1 part (g)). Hence the first and second hydrophobic domains serve as cleavable signal peptide and transmembrane domain, respectively, in agreement with the type I transmembrane protein model of Vacher and colleagues (28) (FIG. 1 part (b)).

Figure 2:
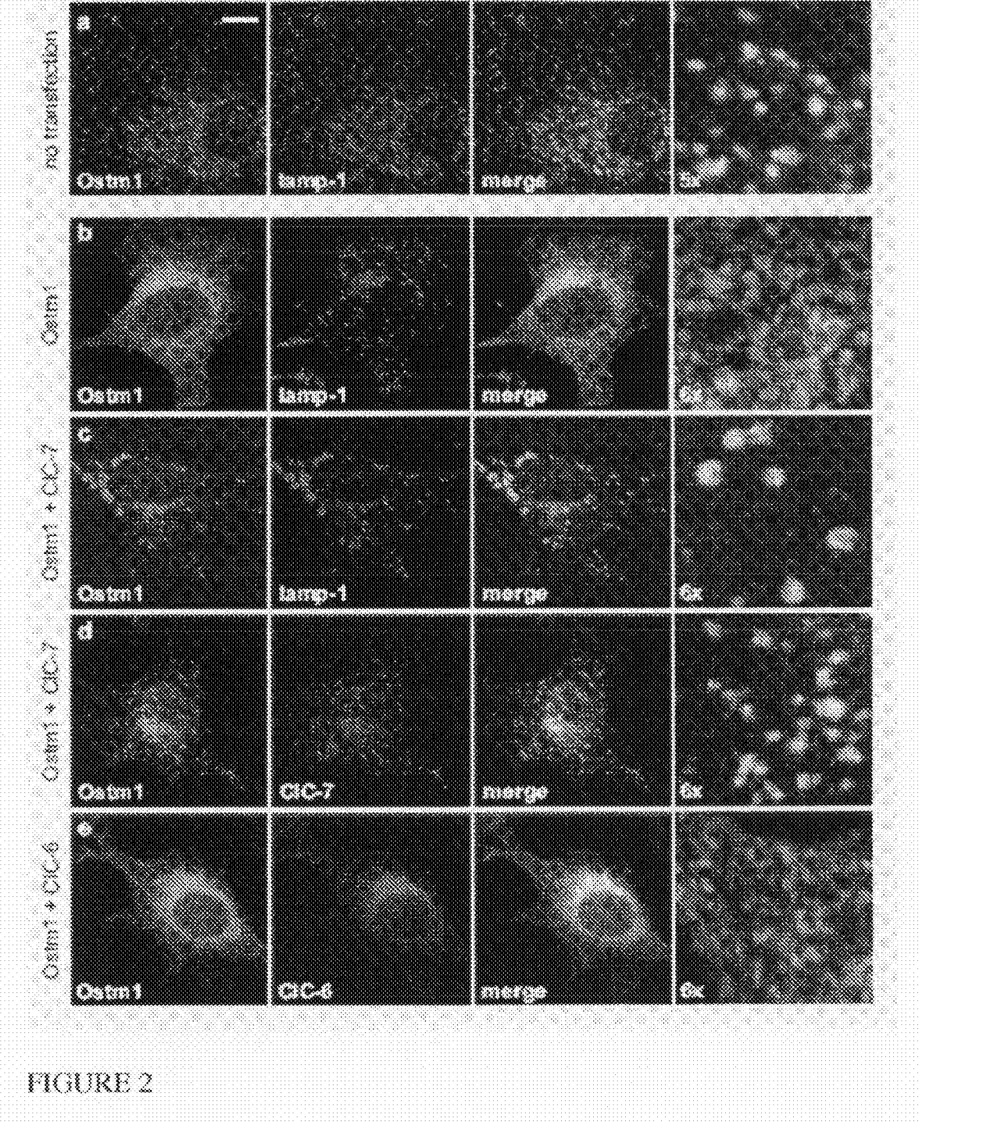
FIG. 2 shows confocal microscopy images from staining fibroblasts for Ostm1, ClC- and lamp-1 proteins. The rows are as follows.

Turning to the results shown in FIG. 2, it is seen that in cultured primary fibroblasts, Ostm1 co-localised with lamp-1, a marker for late endosomes and lysosomes (FIG. 2a). This localisation resembled that of ClC-7, loss of which also causes osteopetrosis (22). However, when fibroblasts were transiently transfected with Ostm1 (FIG. 2b), no significant co-localisation with lamp-1 was observed and Ostm1 staining was rather suggestive of the ER. Co-transfection with ClC-7 restored a punctate Ostm1 pattern that largely co-stained for lamp-1 (FIG. 2c) and ClC-7 (FIG. 2d). The effect of ClC-7 was specific, as neither co-transfection with ClC-3 (not shown) nor with ClC-6 (FIG. 2e), both expressed in the endosomal/lysosomal pathway (12, 47), resulted in such changes.

Figure 3:
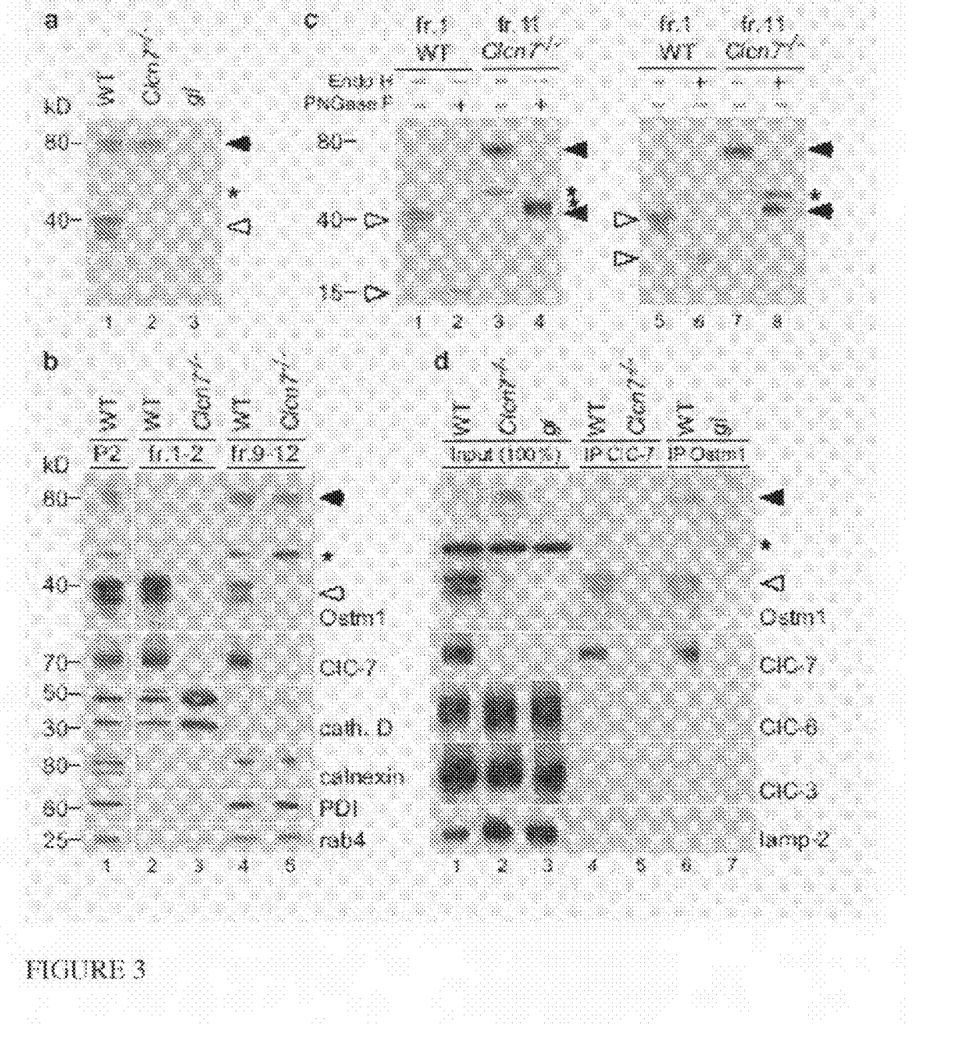
FIG. 3 shows Western blots as follows.

As ClC-7 changed Ostm1 localisation, we studied Ostm1 in ClC-7 knockout (Clcn7$^{-/-}$) mice. Western blots surprisingly indicated an exclusive loss of the 35-45 kD Ostm1 doublet Clcn7$^{-/-}$ brain (FIG. 3 part (a)). Subcellular fractionation of WT brain revealed that the small Ostm1 form was co-enriched with lysosomal markers (bottom fractions, 1-2), whereas the 80 kpa form was only detectable in fractions 9-12 containing markers for endosomes and the ER (FIG. 3 part (b)). Such experiments provided samples only containing the small (WT fractions containing lysosomes) or large (Clcn7$^{-/-}$ fractions containing endosomes/ER) Ostm1 forms which were used for deglycosylation. PNGaseF reduced the size of both species (FIG. 3 part (c), lanes 2 and 4), while only the 35-45 kD form was partially resistant to EndoH (FIG. 3 part (c), compare lanes 2 and 6). This indicated that the small, but not the large species had left the ER. Our results thus show that ClC-7 is needed to traffic Ostm1 from the ER to lysosomes, and that the luminal domain of Ostm1 is cleaved on its way to, or in, this final compartment.

Figure 6:
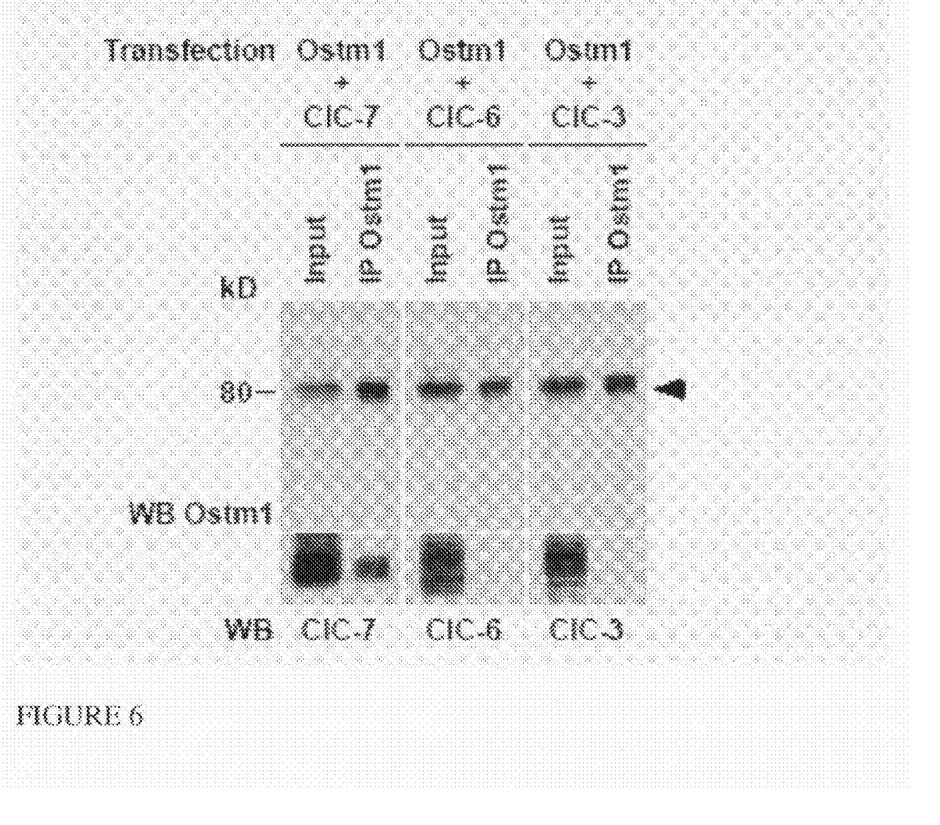
FIG. 6 is a Western blot demonstrating that an ~80 kDa Ostm1 species interacts with ClC-7 in transfected HEK cells, whereas ClC-3 and ClC-6 do not interact with Ostm1.

ClC-7 could be efficiently co-immunoprecipitated from brain with Ostm1, and vice versa (FIG. 3 part (d)). This interaction was specific, since it was neither observed with the related endosomal ClC-3 and ClC-6 proteins, nor with lamp-2. As expected from the lysosomal localisation of ClC-7 (30), antibodies against ClC-7 almost exclusively precipitated the cleaved, lysosomal Ostm1 fragment from brain. Co-immunoprecipitation performed with transfected cells, in which only the large form could be detected, showed that this putative ER form also interacted with ClC-7 (FIG. 6). Surprisingly, FIG. 3 part (d) also revealed that ClC-7 levels were drastically reduced in extracts of gl brain (lane 3).

Figure 4:
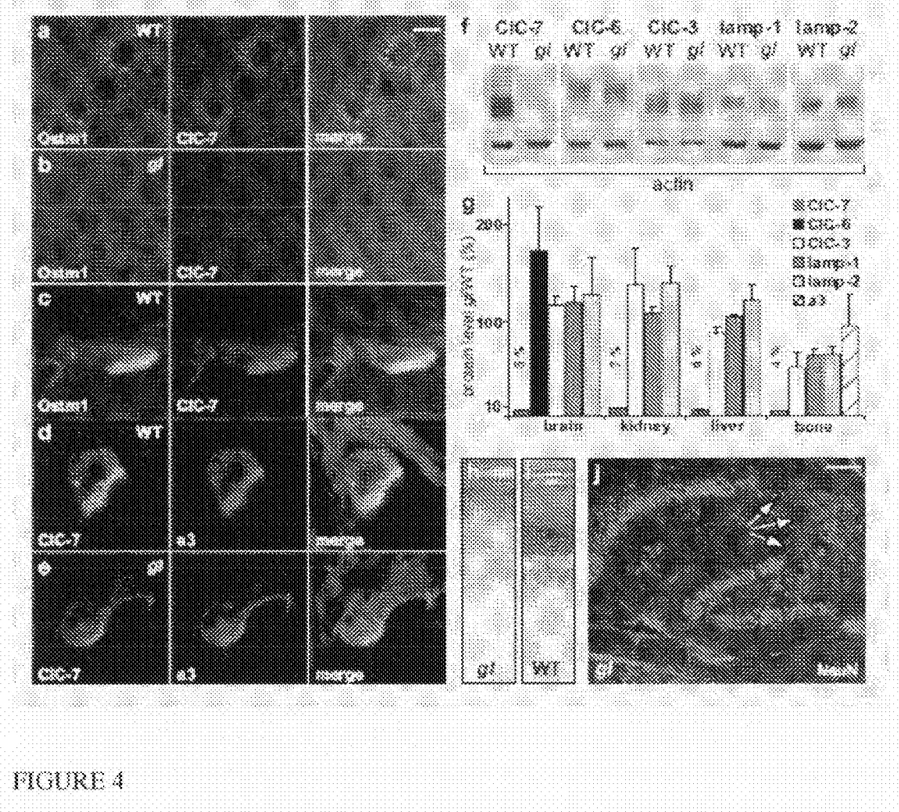

Both ClC-7 and Ostm1 are expressed in many tissues, including brain, liver, kidney, and osteoclasts (22, 28, 30, 44, 48). Immunohistochemistry of brain sections revealed that both proteins co-localised in neuronal cell bodies in structures that most likely represent late endosomes/lysosomes (30) (FIG. 4a). In grey-lethal (gl) neurons (FIG. 4b), both proteins were undetectable. Both proteins also co-localised in osteoclasts in a pattern that represents the 'ruffled border' (FIG. 4c). This acid-secreting plasma membrane domain was identified by co-staining for the a3 proton pump subunit (FIG. 4d) (49), mutations in which also underlie osteopetrosis (50-54).

In line with our Western blot analyses (FIG. 3 parts (a,b,d)), Ostm1 staining was very weak in Clcn7$^{-/-}$ mice while ClC-7 labelling was drastically reduced in grey-lethal cells. These cells included neurons (FIG. 4b) and osteoclasts (FIG. 4e), in which the remaining portion of ClC-7 still localised to the ruffled border. Western blots revealed a strong decrease of ClC-7, but not of ClC-3, ClC-6, lamp-1 and lamp-2 in gl brain (FIG. 4f). Quantification of Western blots from brain, kidney, liver and bone showed a decrease in gl mice of ClC-7, but not of other late endosomal/lysosomal proteins tested (ClC-3, ClC-6, lamp-1/-2, H$^+$-ATPase a3, FIG. 4g). The moderate decrease of control proteins in bone may be explained by the osteopetrosis of gl mice. This Western blot analysis revealed that ClC-7 was reduced to less than 10% in gl mice (FIG. 4f,g). Neither the transcript level of ClC-7 in g/tissues nor that of Ostm1 in Clcn7$^{-/-}$ mice was changed (not shown).

ClC-7 may support bone resorption by electrically shunting the H$^+$-ATPase that acidifies the osteoclast resorption lacuna (22), or by similarly facilitating the insertion of proton-pump containing vesicles into the ruffled border, which is underdeveloped in both Clcn7$^{-/-}$ and gl osteoclasts (22, 45). This mechanism is also feasible if ClC-7 were not a Cl$^-$-channel, as believed so far (22, 48), but an electrogenic Cl$^-$/H$^+$-exchanger like ClC-ec1(27), ClC-4 and ClC-5 (23, 26) (23). As the intracellular localisation of ClC-7 precluded biophysical analysis, these alternatives remain untested. Our work suggests that loss of Ostm1 causes osteopetrosis (28, 29, 55) by decreasing the amount of ClC-7 to pathogenic levels. Already a 75% decrease of ClC-7 function by dominant negative mutations causes mild osteopetrosis in humans (20, 53). The even lower levels of ClC-7 in gl mice may suffice to cause the severe osteopetrosis observed with OSTM1 mutations (28, 29, 55).

Known disease-causing mutations in the human OSTM1 gene (28, 29) introduce frame-shifts that replace the Ostm1 polypeptide by short unrelated sequences 143 or 21 residues (28, 29) before the transmembrane domain. When an epitope-tagged construct modelled after the latter mutation (28) (FIG. 1 part (a)) was transfected into cells, co-expression with ClC-7 failed to direct the truncated Ostm1 to lysosomes (data not shown) and the truncated protein was secreted into the supernatant (FIG. 1 part (g)). Thus, this mutant may lead to disease because it no longer interacts with ClC-7.

The phenotypes of Clcn7$^{-/-}$ and gl mice are strikingly similar. On an agouti background, the fur of ClC-7 KO mice is grey (data not shown), just like the coat colour of grey-lethal mice (28, 56). The disruption of ClC-7 not only entails osteopetrosis (22), but also retinal (22, 30) and CNS (22, 30) degeneration that is related to lysosomal storage disease (22, 30). We detected a similar retinal and hippo-campal degeneration in grey-lethal mice (FIG. 4h-j). Like Clcn7$^{-/-}$ mice (30), they displayed electron-dense storage material in neurons and renal proximal tubular cells, possibly pointing to an altered acidification during lysosome formation, or to a role of lysosomal chloride (23, 28). Taken together, the ClC-7/Ostm1 complex is also important for the function of melanocytes and lysosomes. Patients with OSTM1 mutations may develop lysosomal storage disease in addition to osteopetrosis.

Our work has identified Ostm1 as a hitherto unknown ancillary β-subunit of ClC-7. Ostm1 needs ClC-7 to travel to lysosomes, whereas ClC-7 can reach its destination without Ostm1. The stability of ClC-7 depends on its association with Ostm1. As pronounced glycosylation is thought to protect lysosomal membrane proteins from degradation (57, 58), one may speculate that the highly glycosylated Ostm1 protein shields ClC-7, the sole mammalian CLC lacking N-linked glycosylation sites, from lysosomal proteases. The osteopetrosis, lysosomal storage and neurodegeneration observed with a loss of Ostm1 may be entirely explained by a drastic reduction of ClC-7 protein levels.

The invention will be further described and illustrated by the following examples.

EXAMPLE 1

Immunoprecipitation

ClC-7 and Ostm1 can be co-immunoprecipitated using endogenous material (FIG. part (d)) or overexpressed proteins (FIG. 6). As seen in FIG. 3 part (d), ClC-7 was efficiently co-immunoprecipitated from brain with Ostm1, and vice versa Co-immunoprecipitation reveals a ClC-7/Ostm1 complex. Solubilized brain membranes from the genotypes indicated were directly loaded on the gel (input, lanes 1-3), or first immunoprecipitated with ClC-7 (lanes 4,5) or Ostm1 antibodies (lanes 6,7).

Ostm1 or ClC-7 antibodies were crosslinked to protein A sepharose by dimethylpimelimidate. Brain membranes were pelleted and solubilized in lysis buffer (MES buffered saline pH 6.5, 1% Triton X-100, 2.5 mM CaCl$_2$, 2.5 mM MgCl$_2$). Non-solubilized material was removed by centrifugation at 70,000×g. Samples were incubated with protein A sepharose-antibody complexes for 2 h at 4° C. and washed 4× with lysis buffer. After elution with 100 μl 0.1 M glycine/Cl, pH 2.8, samples were neutralized and denatured using SDS sample buffer. Equivalent amounts of lysate and precipitate were separated by SDS-PAGE.

Resulting Western blots were probed for the proteins indicated at right. Arrowheads, specific Ostm1 bands; *, non-specific bands. Equivalent amounts of lysates and precipitates were loaded.

Repetition of this in the presence of a test compound would screen such a compound for the ability to disrupt ClC-7 to Ostm1 binding.

With reference to FIG. 6, Ostm1 was transiently co-expressed with the indicated ClC proteins in HEK293 cells using calcium phosphate precipitation. After 24 to 48 hours, the cells were harvested in HBS pH7.4, pelleted at 1000×g and lysed in HBS containing 1% Triton X-100, 2.5 mM of each MgCl$_2$ and CaCl$_2$ and complete (Roche) protease inhibitors. The supernatant of a 20000×g spin was used for co-immunoprecipitation. Antibodies against Ostm1 were incubated with protein A sepharose in PBS for one hour at room temperature under agitation. They were washed twice with 0.2 M Na-borate pH9 followed by crosslinking the antibodies to the protein A sepharose with 5.2 mg/ml dimethylpimelimidate (Pierce) in borate buffer for 30 min. The reaction was stopped by washing with 0.2 M glycine/Cl PH2.5. Protein samples were incubated with crosslinked antibodies for 2 hours at 4 degrees C. and unbound material was removed by washing 4 times with 1 ml lysis buffer. Bound proteins were eluted with 100 ml of 0.1 M glycine/Cl pH 2.8, neutralized and denatured using SDS sample buffer. The samples were analysed by Western-blotting against Ostm1 and the various ClCs.

When Ostm1 was immunoprecipitated, ClC-7 was co-precipitated, whereas ClC-3 and ClC-6 did not co-precipitate with Ostm1.

Repetition of this in the presence of a test compound would screen such a compound for the ability to disrupt ClC-7 to Ostm1 binding.

EXAMPLE 2

His Tag Precipitation: Detection by Antibody a. Protein Production

The full length ClC-7 cDNA (cloned at NB by RT-PCR-sequenced verified and compared to gi|39725672) was cloned into a TOPO (Invitrogen) vector by PCR to remove the ATG and Stop. A myc and a his tag were fused at its C-terminal end by EcoRI cloning into a picZαA vector (Invitrogen).

A new PCR reintroduced the ATG and the PCR fragment was cloned into a TOPOblunt vector (Invitrogen). The EcoRV-SpeI fragment from this clone containing the ClC-7-myc-His construct was cloned into PVL1393 (Stratagene) SmaI-XbaI sites and the sequence of all the ORF was verified (ATG-ClC-7-myc-His-Stop).

The PVL1393-ClC-7-myc-His construct was used to construct a recombinant baculovirus as described in the book:

Baculovirus Expression vectors, A manual, O Reilly et al, Oxford University Press 1994. Western-blot using both anti-ClC-7 antibodies (22, 59) and anti-His antibody (Invitrogen) were used to confirm the expression of the protein.

Recombinant expression of Ostm1 is established in a similar way in baculovirus. The full length Ostm-1 (GI: 56699489) was cloned at NB by RT-PCR into a TOPO (Invitrogen) and subsequently into PVL1393 (Stratagene).

Figure 5:
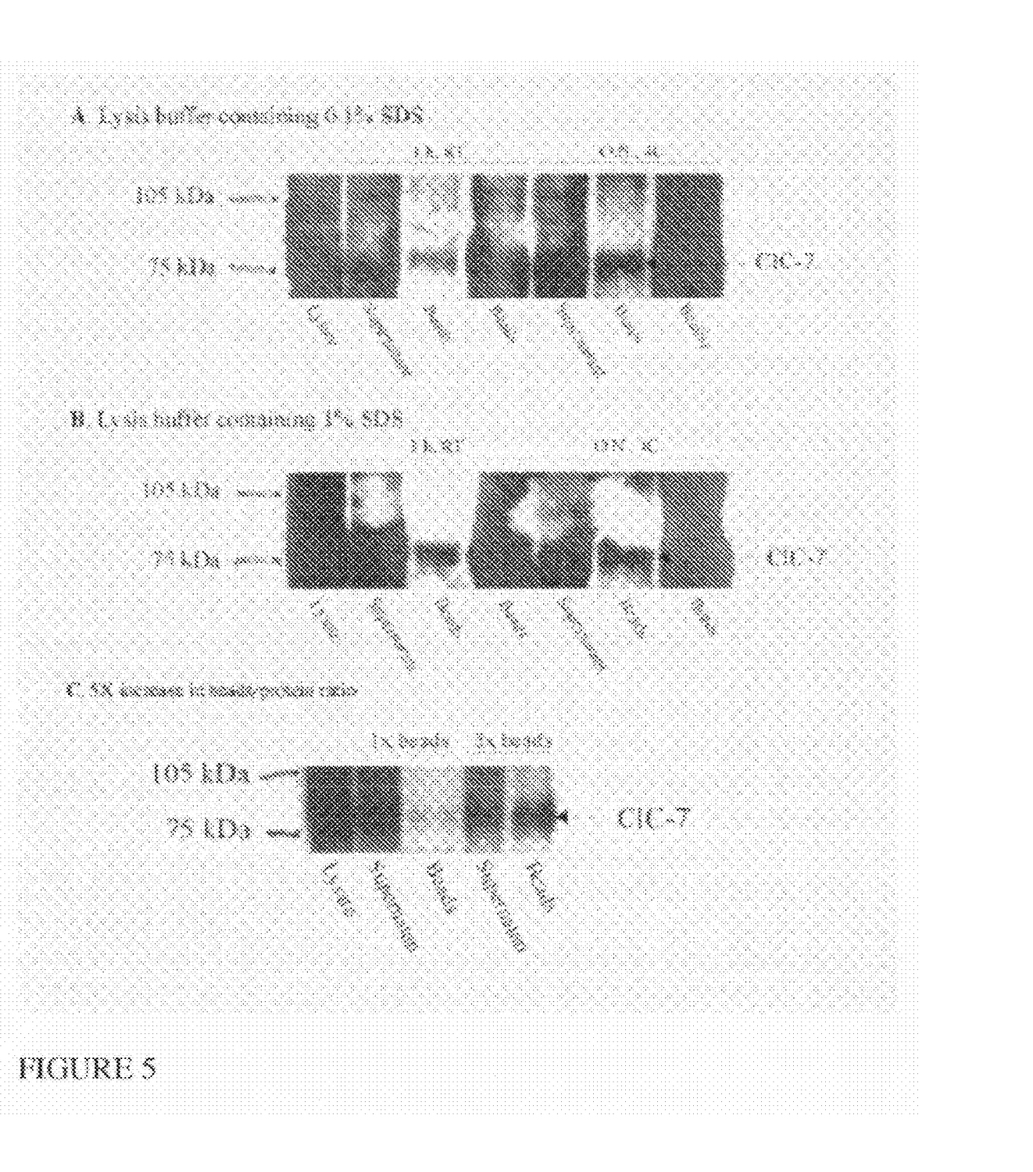
FIG. 5 shows the result of a Western-blot against ClC-7 performed in Example 2, showing that the recombinant ClC-7 expressed in Sf9 cells can be bound to Ni-NTA beads via a His tag.

FIG. 5 illustrates how the recombinant ClC-7 expressed in Sf9 cells can be trapped on Ni-NTA beads. 20-106 Sf9 cells were infected with 1 ml baculovirus for 72 h. Cells were lysed in 5 ml buffer containing Tris HCl 50 mM pH7.5, 150 mM NaCl, protease inhibitor cocktail (Amersham) and 0.1% (A) or 1% (B and C) SDS. 1 ml of lysate was incubated with 200 μl of Ni-NTA beads (Amersham) (A, B and 1×beads C) or 500 μl of Ni-NTA beads (5×beads C) for 1 h at room temperature (RT) (A and B when indicated) or over night at 4° C. (A, B when indicated and C). Cell debris is removed by centrifugation at 20000 rpm. The highest amount of ClC-7 bound to the resin was obtained when incubation was performed over night at 4° C. and when 1% SDS lysis buffer was used. (A, B). Moreover, more ClC-7 was bound to the resin when more resin was used (C).

b. Precipitation

Ni-NTA purification (Invitrogen Manual 021202) is performed using Ni-NTA beads. After preparation of the beads as recommended by the manufacturer, 1 ml of ClC-7 Sf9 cell extract is incubated per 200 μl of Ni-NTA beads overnight at 4° C. The supernatant is removed and 1 ml of the Ostm-1 extract is added for 2 h at 4° C. with the various compounds to test at a concentration of 1 nM. Unbound material is washed by 3 washing with 2 ml of PBS 0.2 mM NaCl-2% CHAPS.

SDS sample denaturing buffer is added to the beads, which are boiled and the samples are run on a gel.

Western-blot against Ostm-1 is performed. If the compound tested is able to disrupt the interaction between ClC-7 and Ostm-1, there will be no signal.

EXAMPLE 3

His Tag Precipitation: Detection by Radioactivity a. Protein Production

The full length ClC-7 cDNA (cloned at NB by RT-PCR-sequenced verified and compared to gi|39725672) was cloned into a TOPO (Invitrogen) vector by PCR to remove the ATG and Stop. A myc and a his tag were fused at its C-terminal end by EcoRI cloning into a picZXA vector (Invitrogen).

A new PCR reintroduced the ATG and the PCR fragment was cloned into a TOPOblunt vector (Invitrogen). The EcoRV-SpeI fragment from this clone containing the ClC-7-myc-His construct was cloned into PVL1393 (Stratagene) SmaI-XbaI sites and the sequence of all the ORF was verified (ATG-ClC-7-myc-His-Stop).

The PVL1393-ClC-7-myc-His construct was used to construct a recombinant baculovirus as described in the book Baculovirus Expression vectors, A manual, 0 Reilly et al, Oxford University Press 1994. Western-blot using both ClC-7 antibodies (22, 59) and his antibody (Invitrogen) was used to confirm the expression of the protein.

Recombinant expression of Ostm1 is established in a similar way in baculovirus. The full length Ostm-1 (GI: 56699489) was cloned at NB by RT-PCR into a TOPO (Invitrogen) and subsequently into PVL1393 (Stratagene).

Sf9 cells are infected with ClC-7 and Ostm1 baculovirus for 48 or 72 h with 1 ml of virus for $20.10^6$ cells in a 175 cm³ flask. 4 h before lysis, a medium without Methionine and Cysteine is added with 20 mCi/ml of $S^{35}$ Met and $S^{35}$ Cys.

The cells are lysed in 1 ml of Tris HCl 50 mM pH7.5, 150 mM, SDS 0.1%, protease inhibitor cocktail (Amersham) and the extract is diluted to 1 mg/ml. Cell debris is removed by a centrifugation at 20000 rpm.

b. Precipitation

Ni-NTA purification (Invitrogen Manual 021202) is performed using Ni-NTA beads. After preparation of the beads as recommended by the manufacturer, 1 ml Sf9 cells extract is incubated per 200 μl of Ni-NTA beads overnight at 4 degrees with the various compounds to test at a concentration of 1 nM. Unbound material is washed by 3 washing with 2 ml of PBS 0.2 mM NaCl-2% CHAPS.

SDS sample denaturing buffer is added to the beads, boiled and the samples are analysed by SDS-page and visualized by autoradiography. This method has been used earlier for other proteins (60).

EXAMPLE 4

Lack of Interaction Between Ostm1 and Chloride Channels Other than ClC-7

Referring again to FIG. 6, Ostm1 was transiently co-expressed with the indicated CLC proteins in HEK293 cells. Upon such overexpression, only the ~80 kD (arrowhead), but not the 35-45 kD Ostm1 species was detected in Western blots. When Ostm1 was immunoprecipitated from transfected cell lysates using the guinea-pig antibody against the carboxyterminus of Ostm1, ClC-7 was co-precipitated. Thus, ClC-7 also interacts with the uncleaved Ostm1 species. By contrast, ClC-6 or ClC-3 could not be co-precipitated, demonstrating the specificity of the ClC-7/Ostm1 interaction.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'.

REFERENCE LIST

1. Rodan, G. A. and Martin, T. J. 2000. Therapeutic approaches to bone diseases. *Science.* 289:1508-1514.
2. Teitelbaum, S. L. and Ross, F. P. 2003. Genetic regulation of osteoclast development and function. *Nat Rev. Genet.* 4:638-649.
3. Teitelbaum, S. L. 2000. Bone resorption by osteoclasts. *Science.* 289:1504-1508.
4. Stenbeck, G. 2002. Formation and function of the ruffled border in osteoclasts. *Semin. Cell Dev. Biol.* 13:285-292.
5. Blair, H. C., Teitelbaum, S. L., Tan, H. L., Koziol, C. M., and Schlesinger, P. H. 1991. Passive chloride permeability charge coupled to H(+)-ATPase of avian osteoclast ruffled membrane. *Am J. Physiol.* 260:C1315-C1324.
6. Blair, H. C., Teitelbaum, S. L., Grosso, L. E., Lacey, D. L., Tan, H. L., McCourt, D. W., and Jeffrey, J. J. 1993. Extracellular-matrix degradation at acid pH. Avian osteoclast acid collagenase isolation and characterization. *Biochem J.* 290 (Pt 3):873-884.
7. Blair, H. C., Teitelbaum, S. L., Ghiselli, R., and Gluck, S. 1989. Osteoclastic bone resorption by a polarized vacuolar proton pump. *Science.* 245:855-857.

8. Blair, H. C., Schlesinger, P. H., Ross, F. P., and Teitelbaum, S. L. 1993. Recent advances toward understanding osteoclast physiology. *Clin Orthop.* 7-22.
9. al Awqati, Q. 1995. Chloride channels of intracellular organelles. *Curr Opin Cell Biol.* 7:504-508.
10. Laitala, T. and Vaananen, H. K. 1994. Inhibition of bone resorption in vitro by antisense RNA and DNA molecules targeted against carbonic anhydrase II or two subunits of vacuolar H(+)-ATPase. *J Clin Invest.* 93:2311-2318.
11. Kiviranta, R., Morko, J., Alatalo, S. L., NicAmhlaoibh, R., Risteli, J., Laitala-Leinonen, T., and Vuorio, E. 2005. Impaired bone resorption in cathepsin K-deficient mice is partially compensated for by enhanced osteoclastogenesis and increased expression of other proteases via an increased RANKL/OPG ratio. *Bone.* 36:159-172.
12. Jentsch, T. J., Poet, M., Fuhrmann, J. C., and Zdebik, A. A. 2005. Physiological functions of CLC Cl– channels gleaned from human genetic disease and mouse models. *Annu. Rev. Physiol.* 67:779-807.
13. Jentsch, T. J., Stein, V., Weinreich, F., and Zdebik, A. A. 2002. Molecular structure and physiological function of chloride channels. *Physiol. Rev.* 82:503-568.
14. Nilius, B., Eggermont, J., Voets, T., and Droogmans, G. 1996. Volume-activated Cl– channels. *Gen. Pharmacol.* 27:1131-1140.
15. Kelly, M. E., Dixon, S. J., and Sims, S. M. 1994. Outwardly rectifying chloride current in rabbit osteoclasts is activated by hyposmotic stimulation. *J. Physiol.* 475:377-389.
16. Sakai, H., Nakamura, F., and Kuno, M. 1999. Synergetic activation of outwardly rectifying Cl– currents by hypotonic stress and external Ca2+ in murine osteoclasts. *J. Physiol.* 515 (Pt 1):157-168.
17. Weidema, A. F., Dixon, S. J., and Sims, S. M. 2000. Electrophysiological characterization of ion channels in osteoclasts isolated from human deciduous teeth. *Bone.* 27:5-11.
18. Campos-Xavier, A. B., Saraiva, J. M., Ribeiro, L. M., Munnich, A., and Cormier-Daire, V. 2003. Chloride channel 7 (CLCN7) gene mutations in intermediate autosomal recessive osteopetrosis. *Hum. Genet.* 112:186-189.
19. Benichou, O., Cleiren, E., Gram, J., Bollerslev, J., de Vernejoul, M. C., and Van Hul, W. 2001. Mapping of autosomal dominant osteopetrosis type II (Albers-Schonberg disease) to chromosome 16p13.3. *Am J. Hum. Genet.* 69:647-654.
20. Cleiren, E., Benichou, O., Van Hul, E., Gram, J., Bollerslev, J., Singer, F. R., Beaverson, K., Aledo, A., Whyte, M. P., Yoneyama, T. et al. 2001. Albers-Schonberg disease (autosomal dominant osteopetrosis, type II) results from mutations in the ClCN7 chloride channel gene. *Hum. Mol Genet.* 10:2861-2867.
21. Daniels, R. J., Peden, J. F., Lloyd, C., Horsley, S. W., Clark, K., Tufarelli, C., Kearney, L., Buckle, V. J., Doggett, N. A., Flint, J. et al. 2001. Sequence, structure and pathology of the fully annotated terminal 2 Mb of the short arm of human chromosome 16. *Hum. Mol Genet.* 10:339-352.
22. Kornak, U., Kasper, D., Bosl, M. R., Kaiser, E., Schweizer, M., Schulz, A., Friedrich, W., Delling, G., and Jentsch, T. J. 2001. Loss of the ClC-7 chloride channel leads to osteopetrosis in mice and man. *Cell.* 104:205-215.
23. Scheel, O., Zdebik, A. A., Lourdel, S., and Jentsch, T. J. 2005. Voltage-dependent electrogenic chloride/proton exchange by endosomal CLC proteins. *Nature.* 436:424-427.
24. Jentsch, T. J., Poet, M., Fuhrmann, J. C., and Zdebik, A. A. 2005. Physiological functions of CLC Cl– channels gleaned from human genetic disease and mouse models. *Annu. Rev. Physiol.* 67:779-807.
25. Jentsch, T. J., Neagoe, I., and Scheel, O. 2005. CLC chloride channels and transporters. *Curr Opin Neurobiol.* 15:319-325.
26. Picollo, A. and Pusch, M. 2005. Chloride/proton antiporter activity of mammalian CLC proteins ClC-4 and ClC-5. *Nature.* 436:420-423.
27. Accardi, A. and Miller, C. 2004. Secondary active transport mediated by a prokaryotic homologue of ClC Cl– channels. *Nature.* 427:803-807.
28. Chalhoub, N., Benachenhou, N., Rajapurohitam, V., Pata, M., Ferron, M., Frattini, A., Villa, A., and Vacher, J. 2003. Grey-lethal mutation induces severe malignant autosomal recessive osteopetrosis in mouse and human. *Nat Med.* 9:399-406.
29. Ramirez, A., Faupel, J., Goebel, I., Stiller, A., Beyer, S., Stockle, C., Hasan, C., Bode, U., Kornak, U., and Kubisch, C. 2004. Identification of a novel mutation in the coding region of the grey-lethal gene OSTM1 in human malignant infantile osteopetrosis. *Hum. Mutat.* 23:471-476.
30. Kasper, D., Planells-Cases, R., Fuhrmann, J. C., Scheel, O., Zeitz, O., Ruether, K., Schmitt, A., Poet, M., Steinfeld, R., Schweizer, M. et al. 2005. Loss of the chloride channel ClC-7 leads to lysosomal storage disease and neurodegeneration. *EMBO J.* 24:1079-1091.
31. Van Der Hee, R. M., Deurholt, T., Gerhardt, C. C., and De Groene, E. M. 2005. Comparison of 3 AT1 receptor binding assays: filtration assay, ScreenReady Target, and WGA Flashplate. *J. Biomol. Screen.* 10:118-126.
32. Crane, K. and Shih, D. T. 2004. Development of a homogeneous binding assay for histamine receptors. *Anal Biochem.* 335:42-49.
33. Sorensen, P., Kussmann, M., Rosen, A., Bennett, K. L., Thrige, D. G., Uvebrant, K., Walse, B., Roepstorff, P., and Bjork, P. 2004. Identification of protein-protein interfaces implicated in CD80-CD28 costimulatory signaling. *J. Immunol.* 172:6803-6809.
34. Cooper, M. A. 2003. Label-free screening of bio-molecular interactions. *Anal Bioanal. Chem.* 377:834-842.
35. Parker, G. J., Law, T. L., Lenoch, F. J., and Bolger, R. E. 2000. Development of high throughput screening assays using fluorescence polarization: nuclear receptor-ligand-binding and kinase/phosphatase assays. *J. Biomol. Screen.* 5:77-88.
36. Seethala, R. 2000. Fluorescence polarization competition immunoassay for tyrosine kinases. *Methods.* 22:61-70.
37. Rigler, R., Pramanik, A., Jonasson, P., Kratz, G., Jansson, O. T., Nygren, P., Stahl, S., Ekberg, K., Johansson, B., Uhlen, S. et al. 1999. Specific binding of proinsulin C-peptide to human cell membranes. *Proc Natl. Acad Sci U.S.A.* 96:13318-13323.
38. Liu, Y. C., Huang, V., Chao, T. C., Hsiao, C. D., Lin, A., Chang, M. F., and Chow, L. P. 2005. Screening of drugs by FRET analysis identifies inhibitors of SARS-CoV 3CL protease. Biochem *Biophys Res Commun.* 333:194-199.
39. Klostermeier, D., Sears, P., Wong, C. H., Millar, D. P., and Williamson, J. R. 2004. A three-fluorophore FRET assay for high-throughput screening of small-molecule inhibitors of ribosome assembly. *Nucleic Acids Res.* 32:2707-2715.
40. Sharma, B., Deo, S. K., Bachas, L. G., and Daunert, S. 2005. Competitive binding assay using fluorescence resonance energy transfer for the identification of calmodulin antagonists. *Bioconjug. Chem.* 16:1257-1263.

41. Zhang, B. 2004. Design of FRET-based GFP probes for detection of protease inhibitors. *Biochem Biophys Res Commun.* 323:674-678.
42. Tahtaoui, C., Guillier, F., Klotz, P., Galzi, J. L., Hibert, M., and Ilien, B. 2005. On the Use of Nonfluorescent Dye Labeled Ligands in FRET-Based Receptor Binding Studies. *J Med Chem.* 48:7847-7859.
43. Pramanik, A. and Rigler, R. 2001. Ligand-receptor interactions in the membrane of cultured cells monitored by fluorescence correlation spectroscopy. *Biol Chem.* 382:371-378.
44. Fischer, T., De Vries, L., Meerloo, T., and Farquhar, M. G. 2003. Promotion of G alpha i3 subunit down-regulation by GIPN, a putative E3 ubiquitin ligase that interacts with RGS-GAIP. *Proc Natl. Acad Sci U.S.A.* 100:8270-8275.
45. Rajapurohitam, V., Chalhoub, N., Benachenhou, N., Neff, L., Baron, R., and Vacher, J. 2001. The mouse osteopetrotic grey-lethal mutation induces a defect in osteoclast maturation/function. *Bone.* 28:513-523.
46. Pickart, C. M. 2001. Mechanisms underlying ubiquitination. *Annu. Rev. Biochem.* 70:503-533.
47. Stobrawa, S. M., Breiderhoff, T., Takamori, S., Engel, D., Schweizer, M., Zdebik, A. A., Bosl, M. R., Ruether, K., Jahn, H., Draguhn, A. et al. 2001. Disruption of ClC-3, a chloride channel expressed on synaptic vesicles, leads to a loss of the hippocampus. *Neuron.* 29:185-196.
48. Brandt, S. and Jentsch, T. J. 1995. ClC-6 and ClC-7 are two novel broadly expressed members of the CLC chloride channel family. *FEBS. Lett.* 377:15-20.
49. Nishi, T. and Forgac, M. 2000. Molecular cloning and expression of three isoforms of the 100-kDa a subunit of the mouse vacuolar proton-translocating ATPase. *J Biol Chem.* 275:6824-6830.
50. Scimeca, J. C., Franchi, A., Trojani, C., Parrinello, H., Grosgeorge, J., Robert, C., Jaillon, O., Poirier, C., Gaudray, P., and Carle, G. F. 2000. The gene encoding the mouse homologue of the human osteoclast-specific 116-kDa V-ATPase subunit bears a deletion in osteosclerotic (oc/oc) mutants. *Bone.* 26:207-213.
51. Li, Y. P., Chen, W., Liang, Y., Li, E., and Stashenko, P. 1999. Atp6i-deficient mice exhibit severe osteopetrosis due to loss of osteoclast-mediated extracellular acidification. *Nat Genet.* 23:447-451.
52. Frattini, A., Pangrazio, A., Susani, L., Sobacchi, C., Mirolo, M., Abinun, M., Andolina, M., Flanagan, A., Horwitz, E. M., Mihci, E. et al. 2003. Chloride channel ClCN7 mutations are responsible for severe recessive, dominant, and intermediate osteopetrosis. *J Bone Miner Res.* 18:1740-1747.
53. Frattini, A., Orchard, P. J., Sobacchi, C., Giliani, S., Abinun, M., Mattsson, J. P., Keeling, D. J., Andersson, A. K., Wallbrandt, P., Zecca, L. et al. 2000. Defects in TCIRG1 subunit of the vacuolar proton pump are responsible for a subset of human autosomal recessive osteopetrosis. *Nat Genet.* 25:343-346.
54. Kornak, U., Schulz, A., Friedrich, W., Uhlhaas, S., Kremens, B., Voit, T., Hasan, C., Bode, U., Jentsch, T. J., and Kubisch, C. 2000. Mutations in the a3 subunit of the vacuolar H(+)-ATPase cause infantile malignant osteopetrosis. *Hum. Mol Genet.* 9:2059-2063.
55. Quarello, P., Formi, M., Barberis, L., Defilippi, C., Campagnoli, M. F., Silvestro, L., Frattini, A., Chalhoub, N., Vacher, J., and Ramenghi, U. 2004. Severe malignant osteopetrosis caused by a GL gene mutation. *J Bone Miner. Res.* 19:1194-1199.
56. Boyce, B. F. 2003. Bad bones, grey hair, one mutation. *Nat Med.* 9:395-396.
57. Fukuda, M. 1991. Lysosomal membrane glycoproteins. Structure, biosynthesis, and intracellular trafficking. *J Biol Chem.* 266:21327-21330.
58. Eskelinen, E. L., Tanaka, Y., and Saftig, P. 2003. At the acidic edge: emerging functions for lysosomal membrane proteins. *Trends Cell Biol.* 13:137-145.
59. Schaller, S., Henriksen, K., Sveigaard, C., Heegaard, A. M., Helix, N., Stahlhut, M., Ovejero, M. C., Johansen, J. V., Solberg, H., Andersen, T. L. et al. 2004. The chloride channel inhibitor n53736 prevents bone resorption in ovariectomized rats without changing bone formation. *J Bone Miner Res.* 19:1144-1153.
60. Schaller, S., Grandemange, S., Shpakovski, G. V., Golemis, E. A., Kedinger, C., and Vigneron, M. 1999. Interactions between the full complement of human RNA polymerase II subunits. *FEBS. Lett.* 461:253-257.
61. Estevez R, Boettger T, Stein V, Birkenhager R, Otto E, Hildebrandt F, and Jentsch T J. 2002 Barttin is a Cl− channel beta-subunit crucial for renal Cl− reabsorption and inner ear K+ secretion. Nature 414:558-61
62. Zhao, Q., He, Y., Alespeiti, G., and Debnath, A. K. 2004. A novel assay to identify entry inhibitors that block binding of HIV-1 gp120 to CCR5. *Virology.* 326:299-309.

The invention claimed is:

1. A method for screening a test compound for activity in modulating chloride transport via ClC-7 or for activity in modulating subcellular localization of Ostm1, which method comprises contacting a cell expressing ClC-7 and Ostm1 with a test compound and determining whether or to the extent to which the text compound prevents binding of Ostm1 to ClC-7.

2. The method of claim 1, wherein the ClC-7 and Ostm1 are expressed by an intracellular organelle of the cell.

3. The method of claim 1, wherein the ClC-7 and the Ostm1 each bear a label, and the proximity of the said labels is detectable.

4. The method of claim 1, wherein the Ostm1 is a mammalian Ostm1.

5. The method of claim 4, wherein the Ostm1 is murine Ostm1 or human Ostm1.

6. The method of claim 1, wherein the ClC-7 is a mammalian ClC-7.

7. The method of claim 6, wherein the ClC-7 is murine ClC-7 or human ClC-7.

8. A method for screening a test compound for activity in modulating chloride transport via ClC-7 or for activity in modulating subcellular localization of Ostm1, which method comprises exposing a complex of ClC-7 and Ostm1 formed in situ in a cell or intracellular organelle to a test compound and determining whether or the extent to which the test compound prevents binding of Ostm1 to ClC-7.

9. The method of claim 8, wherein the ClC-7 and Ostm1 are expressed by an intracellular organelle.

10. The method of claim 8, wherein the ClC-7 and the Ostm1 each bear a label, and the proximity of the said labels is detectable.

11. The method of claim 8, wherein the Ostm1 is a mammalian Ostm1.

12. The method of claim 11, wherein the Ostm1 is murine Ostm1 or human Ostm1.

13. The method of claim 8, wherein the ClC-7 is a mammalian ClC-7.

14. The method of claim 13, wherein the ClC-7 is murine ClC-7 or human ClC-7.

* * * * *